(12) United States Patent
Tritthart et al.

(10) Patent No.: US 6,242,002 B1
(45) Date of Patent: Jun. 5, 2001

(54) EFFERVESCENT FORMULATIONS

(75) Inventors: Wolfram Tritthart, Wolfsberg/Karinthia; Mario André Piskernig, St. Stefan/Karinthia; Gottfried Kölbl, Völkermakt/Karinthia, all of (AU)

(73) Assignee: Arzneimittelwerk Dresden GmbH (DE)

( * ) Notice: Subject to any disclaimer, the term of this patent is extended or adjusted under 35 U.S.C. 154(b) by 0 days.

(21) Appl. No.: 09/277,393

(22) Filed: Mar. 26, 1999

(30) Foreign Application Priority Data

Mar. 31, 1998 (DE) ................................. 198 14 257

(51) Int. Cl.⁷ ................. A61K 9/16; A61K 9/46
(52) U.S. Cl. ............ 424/466; 424/435; 424/465; 424/489; 514/770; 514/777; 514/778; 514/784; 514/781
(58) Field of Search .................. 424/464, 465, 424/489, 466, 435

(56) References Cited

U.S. PATENT DOCUMENTS

| | | | |
|---|---|---|---|
| 5,128,145 | 7/1992 | Edgren et al. | 424/473 |
| 5,415,870 * | 5/1995 | Gergely et al. | 424/466 |
| 5,484,608 | 1/1996 | Rudnic et al. | 424/468 |

FOREIGN PATENT DOCUMENTS

| | | |
|---|---|---|
| 34 40 288 A1 | 5/1986 | (DE) . |
| 0 396 335 A1 | 11/1990 | (EP) . |
| 0 406 488 A1 | 1/1991 | (EP) . |
| 0 509 761 A1 | 10/1992 | (EP) . |
| 593807A1 | 10/1992 | (EP) . |
| 0 521 388 A1 | 1/1993 | (EP) . |
| 0 582 186 A1 | 2/1994 | (EP) . |
| 0 617 515 A2 | 9/1994 | (EP) . |
| 89/09051 | 10/1989 | (WO) . |
| 93/00058 | 1/1993 | (WO) . |
| 93/00886 | 1/1993 | (WO) . |
| 94/00124 | 1/1994 | (WO) . |
| 94/17792 | 8/1994 | (WO) . |
| 94/22435 | 10/1994 | (WO) . |
| 94/23707 | 10/1994 | (WO) . |
| 9612472A1 | 10/1994 | (WO) . |
| 94/26218 | 11/1994 | (WO) . |
| 95/07070 | 3/1995 | (WO) . |
| 95/13130 | 5/1995 | (WO) . |
| 95/18603 | 7/1995 | (WO) . |
| 95/34283 | 12/1995 | (WO) . |
| 96/01612 | 1/1996 | (WO) . |
| 96/02239 | 2/1996 | (WO) . |
| 97/17067 | 5/1997 | (WO) . |

* cited by examiner

*Primary Examiner*—James M. Spear
(74) *Attorney, Agent, or Firm*—Gabriel P. Katona LLP

(57) ABSTRACT

The invention relates to an effervescent, rapidly disintegrating oral dosage form of (a) an alkali-sensitive active ingredient, (b) an effervescent base comprising at least one of (i) at least one alkaline earth metal carbonate, (ii) an organic edible acid, and (iii) an alkali metal salt of citric acid, and optionally (c) a pharmaceutically acceptable auxiliary ingredient, and to a process for preparing the dosage form.

22 Claims, 3 Drawing Sheets

Comparison of different effervescent selegiline systems

Test conditions:
aluminium tube, 40°C/75% relative atmospheric humidity

EFFERVESCENT FORMULATIONS

FIELD OF THE INVENTION

The invention relates to solid, rapidly disintegrating oral dosage forms for pharmaceutical administration as effervescent formulations for alkali-sensitive active ingredients, such as selegiline, and to a process for their preparation.

BACKGROUND

The (−) form of deprenyl, also known as selegiline (phenylisopropyl-methylpropynylamine) or its pharmaceutically acceptable salts, are used in the form of tablets as an antiparkinsonian drug.

A large number of forms for administration of selegiline have been described in the patent literature. Transdermal administration forms including, for example, patches, are disclosed in European patents Nos. 404 807; 406 488; 509 761; 591 432; 593 807; 617 515; 647 137; 683 668; 655 900; WO 96/02239; WO 95/18603; and WO 94/23707.

Drug forms for the controlled release of selegiline, for example in the form of tablets, are described in European patent No. 582 186; in WO 96/01612; and in U.S. Pat. No. 5,484,608, and osmotically acting release systems are described in U.S. Pat. No. 5,128,145; and normal-release oral formulations are described in WO 96/22435.

Patent application WO 96/12472 discloses a liposomal composition which comprises the active ingredient selegiline.

Buccal and sublingual forms of administration are disclosed in WO 97/-17067. WO 95/07070 describes effervescent formulations which, to avoid the insoluble residues of tricalcium citrate which can be formed when effervescent formulations are dissolved, comprise at least two different edible acids.

WO 93/00886 describes effervescent tablets having good storage stability, for example alkali-sensitive active ingredients such as acetylcysteine, captopril and minoxidil. The tablets comprise an effervescent base containing a solid edible organic acid as carrier crystals, an alkali metal carbonate or bicarbonate and an alkali metal salt of the acid. Two layers are applied onto the carrier crystals. The first layer contains a different acid than the carrier crystals, and the second layer contains the alkali metal salt of one of the two acids.

Selegiline is unstable in alkali-containing effervescent formulations. Even a multilayer construction is not sufficient for stabilization. Alkali carbonates and bicarbonates are more basic than alkaline earth carbonates, such as calcium carbonate. There are no suitable effervescent formulations known for selegiline, which is an alkali-sensitive active ingredient. This may partly be due to the fact that such formulations were so far not successful due to the instability of selegiline, as also shown in FIG. 1.

The therapeutic treatment of various disorders requires, in particular in elderly people, a very frequent and in many cases even the permanent taking of pharmaceuticals.

Parkinson patients usually have problems due to strong tremor when swallowing tablets with liquids. Likewise, taking of tablets is very difficult for patients that have difficulties swallowing.

Therefore there is a need for novel solid, rapidly disintegrating oral dosage forms of administration, particularly effervescent formulations in the form of soluble tablets, buccal tablets or soluble granules which ensure easy administration, even for example, for elderly patients.

BRIEF DESCRIPTION OF THE INVENTION

It is an object of the present invention to provide novel and therapeutically advantageous effervescent formulations for selegiline as well as for other alkali-sensitive active ingredients.

The soluble-tablet-formulations of the present invention are also suitable in the combined use with other soluble tablets, such as with L-dopa, and benzerazide as described in European patent No. 521 388.

This object is achieved by the present invention which provides rapidly disintegrating oral dosage forms with or without water as an effervescent formulation comprising an alkali-sensitive active ingredient and an effervescent base of at least one of (i) an alkaline earth metal carbonate, (ii) an organic edible acid, and (iii) an alkali metal salt of citric acid and, optionally, pharmaceutically acceptable auxiliary ingredient.

The present invention provides effervescent formulations in the form of granules, tablets or sachets. The tablets can also be buccal tablets.

A suitable embodiment of the invention involves effervescent formulations of selegiline or its pharmaceutically acceptable salts.

By addition of water to, or contacting such effervescent formulations with saliva, a suspension or solution is formed with $CO_2$ evolution, and the suspension or solution develops a pleasant taste during taking. Here, a rapid release of the active ingredient is of particular importance to ensure a rapid onset of action. This applies particularly to buccal tablets.

BRIEF DESCRIPTION OF THE DRAWINGS

The invention is described with reference being had to the accompanying drawing, wherein.

DETAILED DESCRIPTION

Effervescent formulations are known in the prior art for various active ingredients and vitamins. These effervescent formulations generally include an agent which is capable of releasing $CO_2$, and an agent which induces the release of $CO_2$. Suitable agents capable of releasing $CO_2$ which are used include alkali metal carbonates or alkali metal bicarbonates, such as sodium carbonate and sodium bicarbonate. Alkaline earth metal carbonate formulations are mainly contained in mineral preparations. Suitable agents for inducing $CO_2$ release include edible organic acids, or their acidic salts, which are present in solid form and which can be formulated with the active ingredient and the other auxiliaries to provide granules or tablets, without premature evolution of $CO_2$.

Suitable edible organic acids include, for example, tartaric acid, malic acid, fumaric acid, adipic acid, succinic acid, ascorbic acid, maleic acid or citric acid. Pharmaceutically acceptable acidic salts include, for example, salts of polybasic acids which are present in solid form and in which at least one acid function is present, such as sodium dihydrogen or disodium hydrogen phosphate or the corresponding citrates.

The active ingredients are either present in the effervescent formulation as readily soluble compounds, or they are solubilized by salt formation during the dissolution process. However, it is also possible to disperse poorly soluble active ingredients.

Selegiline hydrochloride is extremely sensitive to the customary effervescent bases such as sodium bicarbonate, sodium carbonate or sodium hydrogen citrate in combination with organic edible acids, such as citric acid or tartaric acid.

Figure 1:
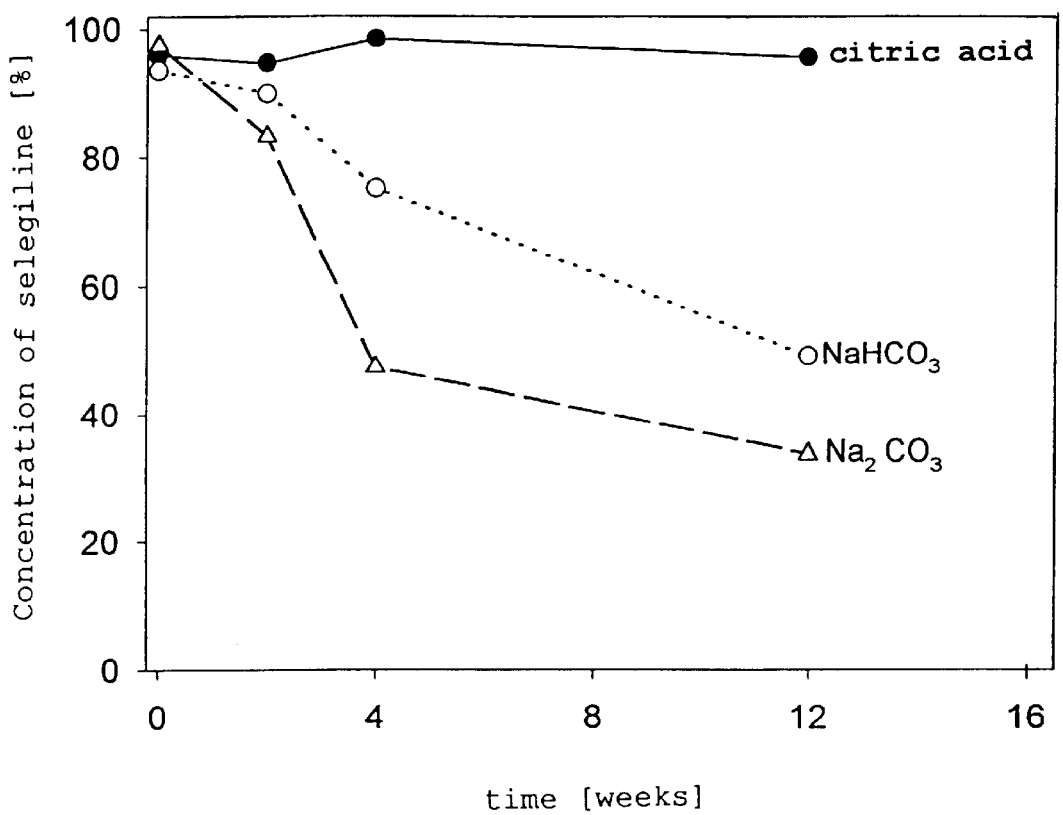
FIG. 1 is a curve showing the alkali instability of selegiline.
Figure 2:
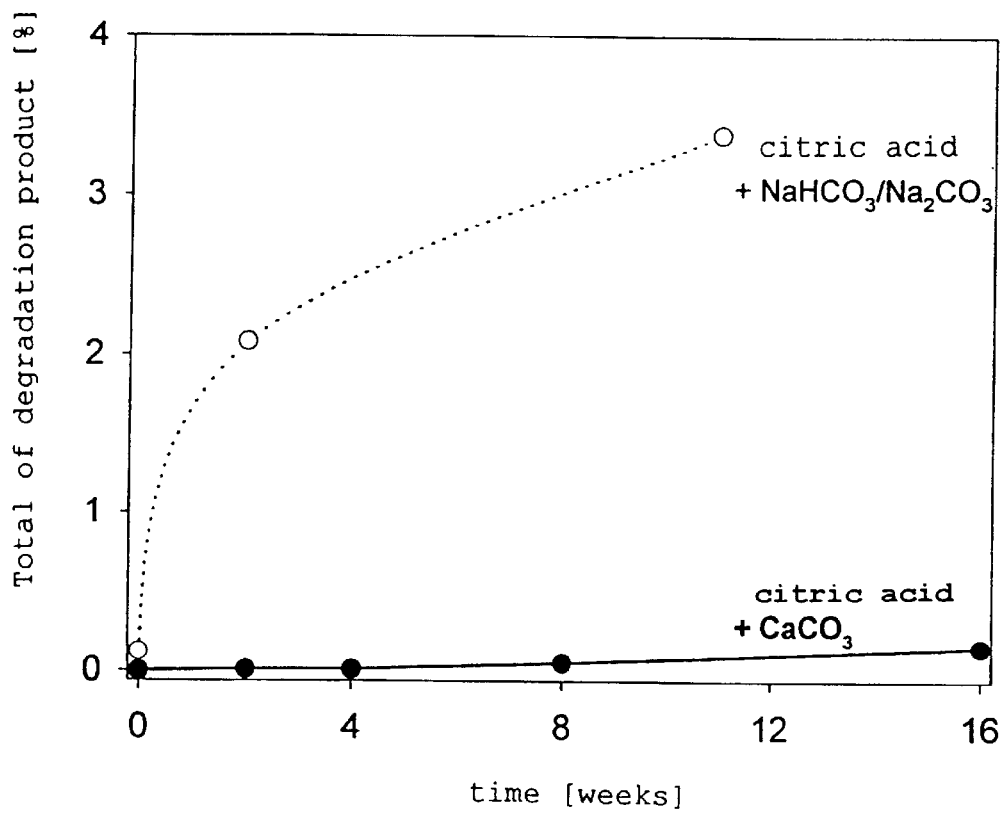
FIG. 2 is a curve comparing the degradation characteristics of different effervescent selegiline compositions.

In these customary effervescent formulations, the selegiline active ingredient is degraded to amphetamine, methamphetamine and demethylselegiline, and the active ingredient undergoes sublimation. It should be noted that degradation to the above mentioned metabolites occurs only partly. The main part of selegiline sublimes in the presence of alkali metal compounds, particularly alkali metal carbonates, so that surprisingly, loss of active ingredient occurs even in the case of only slight metabolization. As can be seen from FIG. 2, the required purity and quantity are no longer met after storage of these effervescent selegiline formulations.

Surprisingly, effervescent formulations based on alkaline earth metals in accordance with the present invention are very stable. Most suitably calcium carbonate and citric acid are used as the effervescent base.

It can be advantageous to have some of the calcium carbonate react with citric acid to give calcium citrate.

Small amounts of sodium citrate do not cause instabilities. However, these amounts may not be more than about 15% of the total weight of the effervescent formulation.

Figure 3:
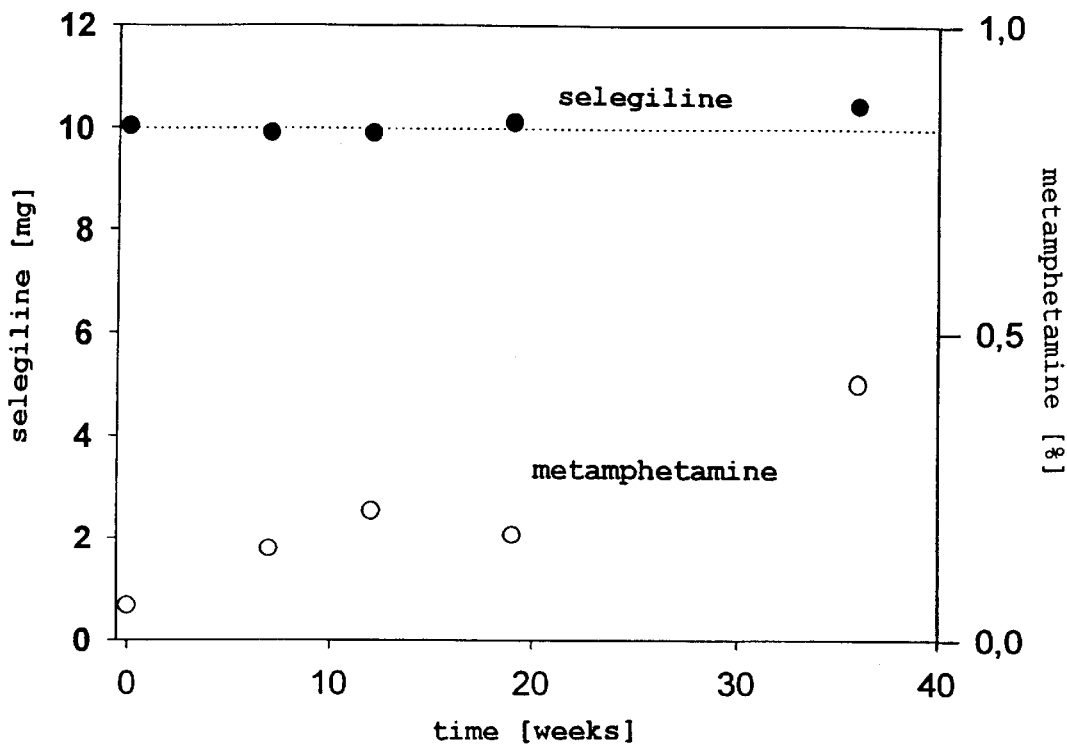
FIG. 3 is a curve showing a stress stability test of selegiline compositions.

At room temperature and even in the stress test at 40° C. and 75% relative atmospheric humidity, the effervescent selegiline formulations according to the present invention show no relevant loss of quality (FIG. 3). This is of particular importance since effervescent formulations have to be well protected against atmospheric humidity during production, filling and storage. Therefore, their preparation is generally carried out only in areas having low atmospheric humidity (Ritschel, Bio Tablette, Echtio Cauher KG 1966, p. 115 f). As discussed by Wells in Pharmaceutical Preformulation (John Wiley publisher, 1988), basic catalysis is in a large number of medicaments a decisive reason for instability.

Although calcium carbonate is known to be used in effervescent tablets but only in cases where calcium therapy is required with calcium as an active ingredient, but not as medicinal excipient for other active ingredients where calcium does not contribute to the therapy. Calcium-containing effervescent tablets are generally employed for treating mineral metabolism problems. Thus, for example WO 95/07070 describes effervescent granules of calcium carbonate and citric acid for producing a pharmaceutical preparation, where 5–20 parts by weight of the citric acid are replaced by at least one other edible acid, such as malic acid.

Calcium carbonate is also employed as additional auxiliary ingredients in pharmaceutical technology, for example as auxiliary ingredients for sugar coating or as extender (Fiedler, Lexikon der Hilfsstoffe, 3rd edition, 1989).

A ready-to-drink solution or suspension with pleasant taste can be prepared with the effervescent formulations of the present invention, suitably in a volume of from 40 to 80 ml of water, which can be easily drunk even in cases of tremor. This also applies to geriatric patients. Buccal or sublingual effervescent preparations are administered directly at the mucosa of the mouth.

Effervescent minitablets can suitably contain from about 5 to about 10 mg of selegiline HCl or other alkali-sensitive active ingredient, and approximately 1200 mg of an effervescent base, while normal effervescent tablets contain from about 2000 mg to about 7000 mg, and buccal preparations suitably contain from about 50 to about 500 mg of an effervescent base. The dose in the buccal preparation can be considerably lower, for example 1–5 mg of e.g. selegiline. In the case of low-dosed active ingredients, the effervescent formulations according to the present invention can comprise up to about 90%, and in the case of high-dosed active ingredients, from about 30% to about 70% of an effervescent base.

The effervescent formulations also permit combined taking together with other active ingredients, as is frequently required in the case of selegiline in Parkinson treatment. Thus, effervescent selegiline formulations can be administered in combination with other soluble tablets, in particular L-dopa/benzerazide combinations or soluble amantadine tablets.

A cocktail treatment, as described in European patent No. 521 388 is also possible. Here, at least two different active ingredients are dissolved or suspended together in an amount of water and are then administered together. Selegiline can also be administered together with vitamin E in effervescent formulations.

As already mentioned, these effervescent preparations of the present invention can also be employed with other alkali-sensitive active ingredients, such as erythromycin, clarithromycin, diazepam, ampicillin, and phenobarbital.

The effervescent formulations according to the present invention can be prepared by conventional processes known in the art. The acids and carbonates are, for example, granulated separately (wet granulation), where the active ingredients are suitably added to the acidic granules. After mixing of the carefully dried granules, soluble lubricants, such as sodium benzoate or polyethylene glycols, are added, and the mixture is compressed.

According to another method, all acids, carbonates and active ingredients are mixed together and heated in a reactor until the citric acid, for example, releases its water of crystallization and granules are formed (see e.g. WO 95/13130). Repeated stirring is required to obtain a uniform material. This is then sieved rapidly and carefully dried. Efficient drying is absolutely necessary to avoid gradual disintegration of the tablets by reaction of the acids with the carbonates.

Vacuum drying cabinets can be used, for example, to achieve rapid drying. In another method of preparation the acid is partially reacted with the basic components, followed by drying under reduced pressure. A soluble lubricant is admixed to the dry granules before compression. However, tableting can also be carried out by using external lubrication.

The effervescent granules that are obtained according to the invention, are then compressed to tablets or filled into sachets.

The alkali-sensitive active ingredient, such as selegiline, is suitably bound to neutral auxiliary ingredients to obtain good homogeneity. Suitable neutral carrier substances for the effervescent formulations according to the invention include lactose, sucrose, sorbitol, mannitol, starch, pectins or cellulose. Other auxiliary ingredients, such as colorants, sugars or sweeteners, can improve the appearance and/or the taste of the aqueous solutions or suspensions obtainable by disintegration of the effervescent tablet.

The use of colorants can serve both for improving the appearance and for identifying the preparation. Suitable colorants which are approved for use in pharmaceuticals include carotenoids and chlorophyl.

Suitable sugars or sweeteners include sucrose, xylitol, D-glucose, sorbitol, mannitol, lactose, aspartame, sodium, saccharin, acelsulfam, and sodium cyclamate.

The following examples illustrate the invention in more detail.

|  | mg |
|---|---|
| Example 1 soluble tablet | |
| Selegiline HCl | 10 |
| MgCO₃ | 96 |
| CaCO₃ | 248 |
| Citric acid | 522 |
| Aspartame | 4 |
| Lactose | 100 |
| Aroma | 15 |
| Total | 995 |
| Example 2 soluble tablet | |
| Selegiline HCl | 10 |
| Calcium carbonate | 310 |
| Citric acid | 620 |
| Aspartame | 7 |
| Aroma | 10 |
| Sodium citrate | 53 |
| Total | 1010 |
| Example 3 soluble tablet | |
| Selegiline HCl | 10 |
| CaCO₃ | 380 |
| Citric acid | 500 |
| Sodium cyclamate | 7 |
| Saccharin sodium | 1 |
| Aroma | 15 |
| Yellow 6 | 1 |
| Total | 914 |
| Example 4 soluble tablet | |
| Selegiline | 5 |
| Calcium carbonate | 331 |
| Citric acid | 625 |
| Aspartame | 10 |
| Aroma | 10 |
| Sodium citrate | 19 |
| Total | 1000 |
| Example 5 effervescent granules | |
| Selegiline HCl | 5 |
| CaCO₃ | 410 |
| Citric acid | 600 |
| Sodium cyclamate | 5 |
| Saccharin sodium | 1 |
| Aroma | 20 |
| Mannitol | 152 |
| Aerosil | 2 |
| Kollidon | 3 |
| Aspartame | 2 |
| Total | 1200 |
| Example 6 soluble tablet | |
| Selegiline HCl | 10 |
| CaCO₃ | 357 |
| Citric acid | 522 |
| Sodium cyclamate | 5.7 |
| Saccharin sodium | 0.9 |
| Aroma | 15 |
| Mannitol | 187 |
| Aerosil | 2 |
| Kollidon | 2 |

-continued

|  | mg |
|---|---|
| Aspartame | 2 |
| Yellow 6 | 1 |
| Sodium citrate | 100 |
| Total | 1204.6 |
| Example 7 soluble tablet | |
| Selegiline HCl | 5 |
| MgCO₃ | 100 |
| CaCO₃ | 320 |
| Citric acid | 450 |
| Aspartame | 3 |
| Lactose | 50 |
| Aroma | 15 |
| Total | 943 |
| Example 8 buccal tablet | |
| Selegiline HCl | 5 |
| Calcium carbonate | 250 |
| Citric acid | 112 |
| Aspartame | 4 |
| Aroma | 10 |
| Sodium citrate | 30 |
| Total | 411 |
| Example 9 buccal tablet | |
| Selegiline HCl | 5 |
| Calcium carbonate | 205 |
| Citric acid | 200 |
| Sodium cyclamate | 2 |
| Saccharin sodium | 0.5 |
| Aroma | 7 |
| Mannitol | 71 |
| Aerosil | 1 |
| Kollidon | 1.3 |
| Aspartame | 1 |
| Total | 493.8 |
| Example 10 effervescent granules | |
| Erythromycin | 500 |
| CaCO₃ | 520 |
| Citric acid | 720 |
| Sodium cyclamate | 7 |
| Saccharin sodium | 1 |
| Aroma | 15 |
| Maize starch | 60 |
| Yellow 6 | 1 |
| Total | 1824 |
| Example 11 effervescent granules | |
| Diazepam | 5 |
| MgCO₃ | 100 |
| CaCO₃ | 320 |
| Citric acid | 450 |
| Aspartame | 3 |
| Lactose | 50 |
| Aroma | 15 |
| Total | 943 |

We claim:

1. An effervescent, rapidly disintegrating oral dosage form, which comprises
   (a) an alkali-sensitive active ingredient,
   (b) an effervescent base, wherein said effervescent base and consists essentially of
      (i) at least one alkaline earth metal carbonate,
      (ii) an organic edible acid, and
      (iii) an alkali metal salt of citric acid, and optionally
   (c) a pharmaceutically acceptable auxiliary ingredient.

2. The dosage form of claim 1, wherein the dosage form comprises a tablet, granules, or sachets, said dosage form being adapted to be dissolved in water before being taken.

3. The dosage form of claim 1, wherein the dosage form comprises a buccal or sublingual tablet adapted to be administered directly into the oral cavity.

4. The dosage form of claims 1, wherein said alkali-sensitive active ingredient is selegiline, erythromycin, clarithromycin, diazepam, ampicillin, phenobarbital, or a pharmaceutically acceptable salt thereof.

5. The dosage form of claim 4, wherein said active ingredient is selegiline or its pharmaceutically effective salt.

6. The dosage form of claim 1, wherein said effervescent base comprises at least one of (i) calcium carbonate, and (ii) magnesium carbonate with citric acid.

7. The dosage form of claim 1 or 6, wherein said effervescent base comprises calcium carbonate and citric acid.

8. The dosage form of claim 1, wherein said effervescent base comprises a maximum of about 15% wt. sodium citrate.

9. The dosage form of claim 1, further comprising vitamin E.

10. The dosage form of claim 1, wherein said effervescent base comprises a maximum of about 90% wt. of the dosage form.

11. The dosage form of claim 1, said alkali-sensitive active ingredient comprises from about 30% wt. to about 70% wt. of said effervescent base.

12. The dosage form of claim 1, wherein the dosage form is an effervescent minitablet comprising from about 5 mg to about 10 mg selegiline HCl, and about 1200 mg of said effervescent base.

13. The dosage form of claim 1, wherein the dosage form is a buccal preparation comprising from about 1 to about 10 mg selegiline HCl, and from about 50 to about 500 mg of said effervescent base.

14. The dosage form of claim 13, wherein said buccal preparation comprises from about 5 to about 10 mg selegiline HCl.

15. The dosage form of claim 1, wherein said auxiliary ingredient comprises at least one of (i) a colorant, and (ii) at least one sweetener.

16. The dosage form of claim 15, wherein said sweetener is at least one of a sucrose, xylitol, D-glucose, sorbitol, mannitol, lactose, aspartame, sodium saccharine, acesulfam, and sodium cyclamate.

17. A process for preparing the dosage form of claim 1, which comprises separately granulating said alkaline earth metal carbonate and said organic edible acid, and adding said alkali-sensitive active ingredient to the acidic granules, and if necessary drying the granules, and mixing the dried granules.

18. The process of claim 17, wherein said alkaline earth metal carbonate comprises at least one of calcium carbonate and magnesium carbonate.

19. The process of claim 17, wherein said alkali-sensitive active ingredient is combined with a neutral carrier therefor.

20. The process of claim 17, wherein said auxiliary ingredient is at least one of lactose, sucrose, sorbitol, mannitol, starch, pectin, or cellulose.

21. The process of claim 17, wherein the dosage form comprises calcium carbonate and citric acid, and a part of said calcium carbonate has been reacted with citric acid to form calcium citrate.

22. A process for preparing the dosage form of claim 1, which comprises mixing all of the active ingredients and of said effervescent base, heating and drying the mixture.

* * * * *